United States Patent [19]

Boileau et al.

[11] Patent Number: 5,377,691
[45] Date of Patent: Jan. 3, 1995

[54] PLURAL-CHARACTERISTIC-MEASURING RADIAL ERECTOMETER

[76] Inventors: Michel A. Boileau, 2275 NE. Doctors Dr., Bend, Oreg. 97701; Matthew W. Hoskins, 10933 SW. 41st Ave., Portland, Oreg. 97219

[21] Appl. No.: 61,443

[22] Filed: May 14, 1993

[51] Int. Cl.$^6$ ............................................. A61B 5/03
[52] U.S. Cl. ................................................ 128/774
[58] Field of Search .............. 128/694, 774; 33/511, 33/512, 514.1

[56] References Cited

U.S. PATENT DOCUMENTS

| | | |
|---|---|---|
| 3,926,184 | 12/1975 | Gehl . |
| 4,428,385 | 1/1984 | Morales ............................. 128/774 |
| 4,469,108 | 9/1984 | Goldstein ........................... 128/774 |
| 4,700,715 | 10/1987 | Levine et al. ...................... 128/774 |
| 4,747,415 | 5/1988 | Lavoisier ........................... 128/774 |
| 4,766,909 | 8/1988 | Timm et al. ....................... 128/774 |
| 4,776,325 | 10/1988 | Etingher . |
| 4,960,131 | 10/1990 | Koss .................................. 128/774 |

OTHER PUBLICATIONS

Snap-Gauge, Impotence Screening Device Brochure, 1983, Dacomed Corporation.

*Primary Examiner*—Max Hindenburg
*Attorney, Agent, or Firm*—Kolisch Hartwell Dickinson McCormack & Heuser

[57] ABSTRACT

A plural-characteristic-measuring radial erectometer is described for use by a male user in connection with treatment for impotency. The erectometer includes elongate band-like structure positionable around the user's flaccid penis and constructed to form a closed loop having a desired circumference corresponding to such penis. Also described is first measurement structure such as a detachable tab formed as one end of the band-like structure, and being manually movable to a first configuration providing an indication that the penis is in the flaccid condition. The detachable tab is also radially changeable to a second configuration as a result of radial-penile forces that will occur when the penis becomes erect. Also described is second measurement structure such as an elongate strip formed as the other end of the band-like structure, and also being manually movable to a first configuration providing an indication that the penis is in the flaccid condition. Like the first measurement structure, the second one is also radially changeable to a second configuration as a result of the radial-penile forces. Correlation between the first and second configurations of the tab and the strip provides an indication that the penis changed from a flaccid condition to an erect condition, and provides a measurement of a plural, different characteristics of that erect condition. Preferred characteristics are penile rigidity and tumescence.

5 Claims, 2 Drawing Sheets

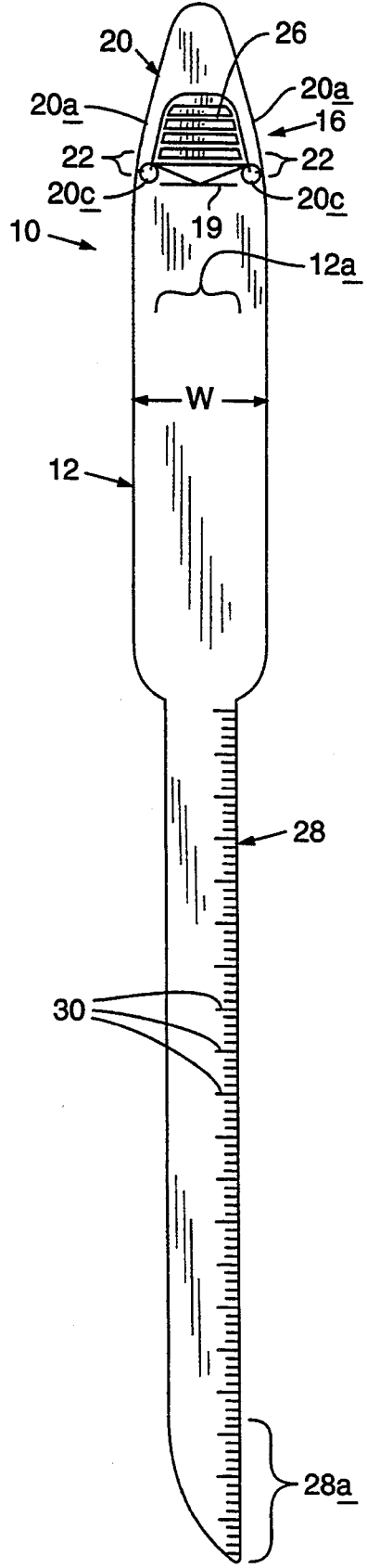
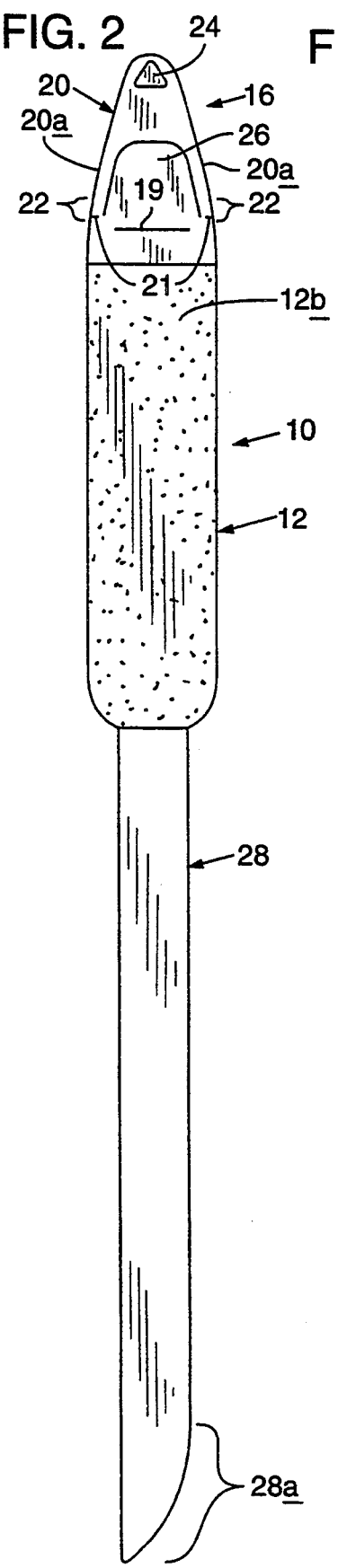
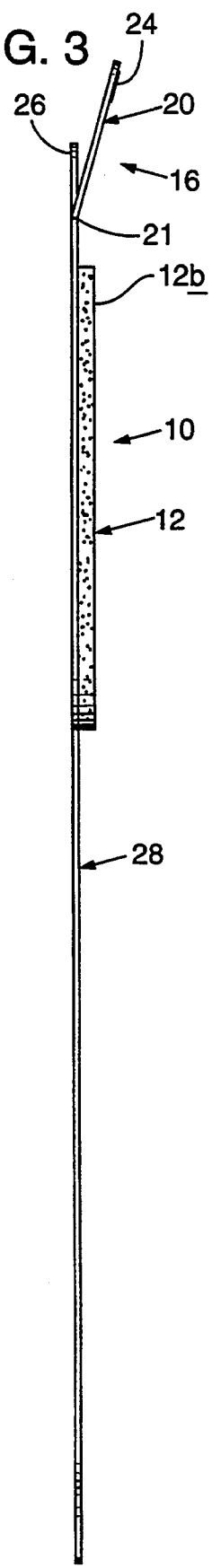

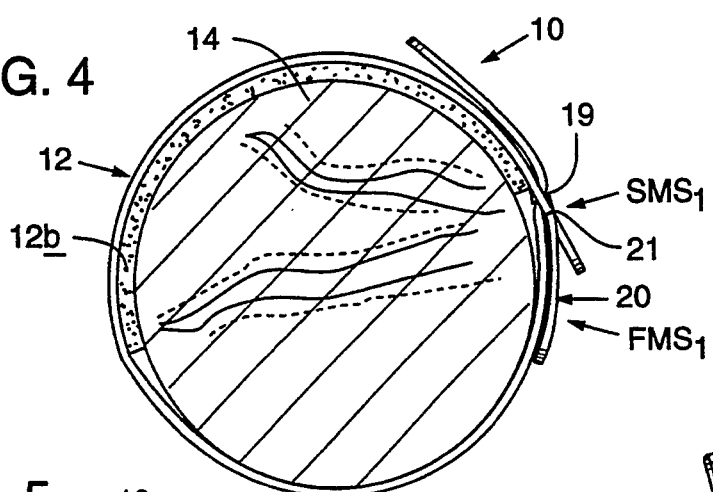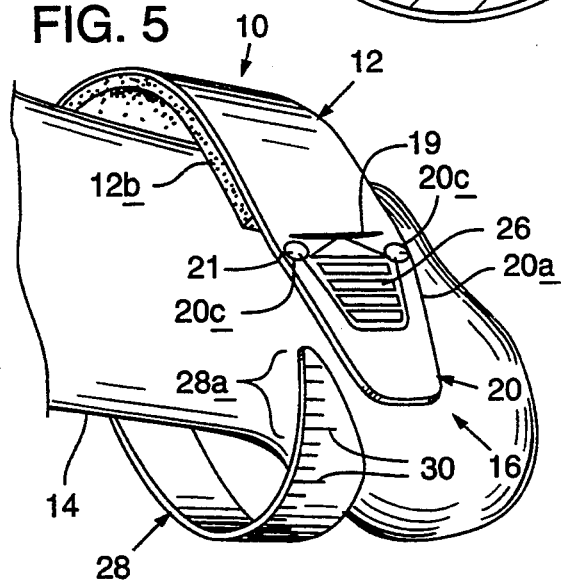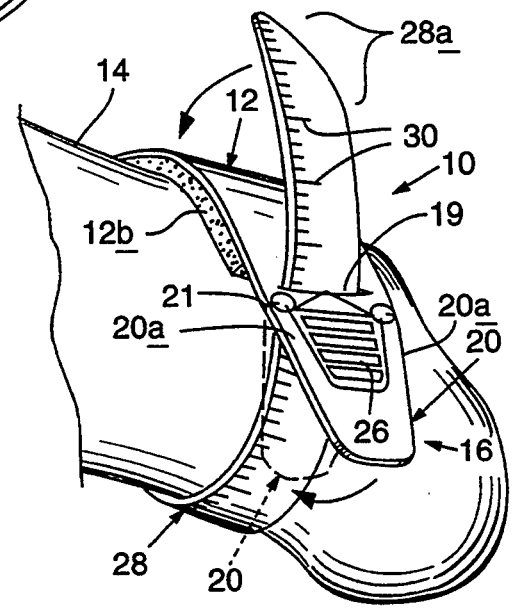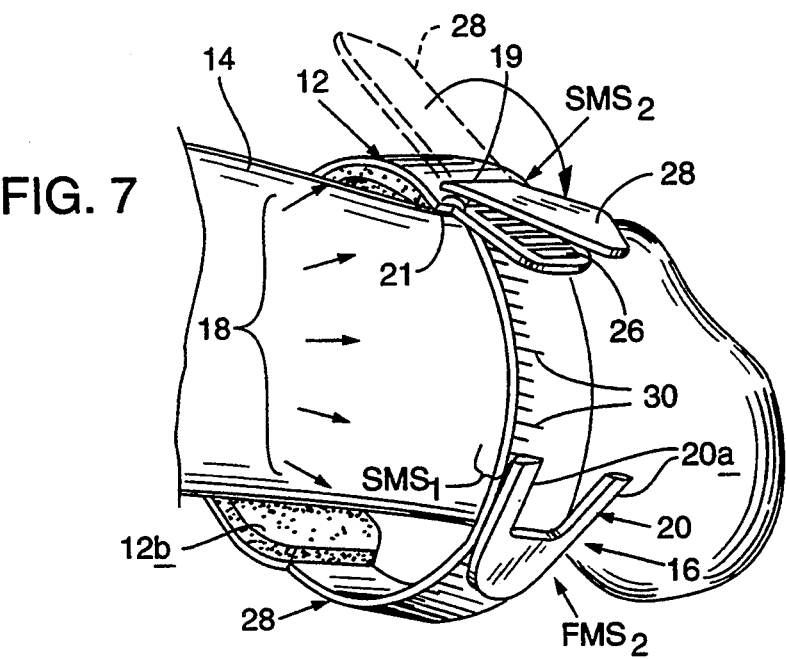

PLURAL-CHARACTERISTIC-MEASURING RADIAL ERECTOMETER

BACKGROUND AND SUMMARY OF THE INVENTION

The invention relates generally to diagnostic devices that are positionable on a penis and usable to identify physiological male impotency from psychological male impotency. More particularly, the invention concerns a novel plural-characteristic-measuring radial erectometer that is constructed for radially measuring plural characteristics of a penile erection, such as penile rigidity and penile tumescence.

Male impotency may occur for either of two basic reasons, a physiological one, or a psychological one. In other words there are two types, "psychological impotency" and "physiological impotency". To treat impotency in a given patient, one must first determine which of the two reasons is the cause for that condition. For obvious reasons, it should be understood that following references to "patient" means a male one.

A known, convenient way to distinguish between the two types of impotency is to observe whether the patient has nocturnal erections in his sleep. Based on various research studies normal males regularly have such sleep erections. Certain research shows that they have approximately two to five such erections per night, depending on a variety of factors including age.

Males with psychological impotency also have such sleep erections. However, males with physiological impotency do not because, due to their particular condition, their bodies cannot achieve an erection at any time.

By reliably observing whether a patient has a sleep erection, one can determine whether he has psychological or physiological impotency. Essentially, if he has a sleep erection, the treating physician knows that the patient's impotency is of the psychological, not physiological type.

Various treatment methods have been developed for identifying whether a patient has a sleep erection. The essential problem is that a patient does not know he is having a sleep erection because it occurs in his sleep, usually his deepest sleep. Early on, conventional treatment involved expensive and undesirable direct observation of a patient during his sleep. The treatment was expensive because it involved hospital stay, and it was undesired because patients did not appreciate its non-private nature.

Some years ago, the first named inventor in the present application was involved with a substantial development in impotency treatment when he and certain colleagues invented the so-called stamp test which involved placing around a patient's flaccid penis a closed ring of stamps, like postage stamps, joined seriatim by perforated regions. The patient could wear such a device at home during his sleep. If he awoke to find the closed ring of stamps was broken open, he knew he had a sleep erection.

Since the invention of the stamp test, there have been numerous conventional proposals for improving and refining the basic test. One refinement involves constructing a device that provides more information than simply that a sleep erection has occurred. For example, the treating physician can also make use of information relating to the character of the sleep erection. There are at least two features of a sleep erection that are useful to the treating physician, one is known as the rigidity of the erection, and the other is known as the tumescence, or increase in circumference, of the penis.

Various conventional proposals have focused on either measuring rigidity or tumescence, but not both. For example, there is an impotency screening device sold by Dacomed Corporation under the trademark SNAP-GAUGE that measures penile rigidity. That device includes a plastic ring that is closed around a patient's flaccid penis. The device is formed with certain plastic elements, each of which will break if a sleep erection having a preselected degree of rigidity occurs.

Representative devices that measure penile tumescence are shown in U.S. Pat. Nos. 4,960,131 to Koss, 4,700,715 to Levine et al., and 4,428,385 to Morales. Each of these devices includes a closed ring fittable around a patient's flaccid penis, and each includes a particular mechanism for measuring tumescence. Those particular mechanisms include an expandable web portion of a ring (Levine et al.), a slider member constructed to allow a portion of a band to be pulled through it (Koss), and a plastic radially expansible loop made with a flexible tube open at ,me end for receiving a tail portion (Morales).

There has been one conventional proposal involving a device for measuring tumescence and rigidity, and it is shown in U.S. Pat. No. 4,469,108 to Goldstein. Goldstein shows a device that includes two radially expansible rings interconnected longitudinally in a spaced relationship by two blades positioned parallel to each other. Each blade is positioned adjacent diametrically opposing locations along the diameter of each ring. Goldstein shows to measure tumescence by the increased radial expansion of the rings, and to measure rigidity by the increase in longitudinal spacing between the rings. Apparently, a sleep erection will cause the rings to move apart as the length of the penis increases. A ratchet-like mechanism of the device maintains the increased spacing of the rings corresponding to the erection, and the radially expansible rings are also constructed to stay in their erection-caused, radially-expanded position.

There are certain drawbacks to the device proposed by Goldstein. For example, its design for measuring rigidity as a function of penile length results in a relatively unwieldy device that is uncomfortable to wear. This drawback is substantial because devices for determining the occurrence of a sleep erection must be extremely comfortable due to their use on an extremely sensitive area of the male body. It is also not clear that measuring penile rigidity as a function of penile length is as useful to the treating physician as by measuring rigidity based on radial-penile forces that act on a closed ring positioned around the penis. Additional patient discomfort may be caused because the device proposed by Goldstein requires that most of the length of the penis will be covered, at least partially, by the device. Further patient-discomfort may be caused when and if the device falls off the patient when his penis returns to a flaccid condition after the sleep erection. The increased, fixed, cylinder-approximating size of the device corresponding to the erect penis will present further patient discomfort because it will be in the patient's way during his sleep. For example, it is likely the patient will roll on the device. When that happens, the device will cause patient discomfort because it will not collapse due to the device's fixed and enlarged condition.

Nowhere has there been shown or suggested to provide a comfortable, reliable device for determining the occurrence of a sleep erection that measures plural characteristics of that erection. Accordingly, it is a principal object of the present invention to provide such a device that overcomes the drawbacks of prior-art devices.

Another object is to provide such a device that provides for reliable, accepted methods of measuring both the rigidity and tumescence of an erect penis.

Yet another object is to provide such a device that is extremely comfortable to wear.

Another important object of the invention is to provide such a device that does not require positioning on a relatively large portion of the penis.

Yet another object is to provide such a device that measures both penile rigidity and tumescence as a function of radial-penile forces caused by the sleep erection.

Still another object is to provide such a device that is easily detachable from the penis after the latter returns to a flaccid condition following a sleep erection.

Yet another object is to provide such a device that is unobtrusive to the patient should it detach during sleep, either inadvertently or because it falls off after the penis returns to its post-sleep-erection, flaccid condition.

It is also an object of the invention to provide such a device that can be easily and cost-effectively manufactured.

In brief summary, one aspect of the invention includes a plural-characteristic-measuring radial erectometer to be worn by a male user. The erectometer includes elongate band-like structure positionable around the user's flaccid penis and constructed to form a closed loop having a desired circumference corresponding to such flaccid penis. Also included is first measurement structure associated with the band-like structure and being manually movable to a first configuration providing an indication that the penis is in a flaccid condition. The first measurement structure is also radially movable to a second configuration as a result of radial-penile forces that will occur when the penis becomes erect. Correlation between the first and second configuration provides an indication that the penis changed from a flaccid condition to an erect condition, and provides a measurement of a first characteristic of that erect condition. That first characteristic is preferably penile rigidity.

The erectometer of the present invention also includes second measurement structure associated with the band-like structure that is manually movable to a first configuration providing an indication that the penis is in the flaccid condition. Like the first measurement structure, the second one is also radially movable to a second configuration as a result of the radial-penile forces. Correlation between the first and second configuration provides an indication that the penis changed from such flaccid condition to an erect condition, and provides a measurement of a second characteristic of that condition. That second characteristic is preferably tumescence.

These and other objects and advantages of the invention will be more clearly understood from a consideration of the accompanying drawings and the following description of the preferred embodiment.

BRIEF DESCRIPTION OF THE DRAWINGS

FIG. 1 is a top plan view showing the preferred embodiment of the erectometer of the present invention.

FIG. 2 is a bottom plan view of the erectometer shown in FIG. 1.

FIG. 3 is a side view of the erectometer shown in FIG. 1.

FIG. 4 is a side view of the erectometer shown in FIG. 1 after it has been placed in use on a patient's flaccid penis, with the latter being shown in cross section.

FIG. 5 is an isometric view showing a first step in positioning the erectometer shown in FIG. 1 on a patient's flaccid penis.

FIG. 6 is an isometric view showing a second step in positioning the erectometer shown in FIG. 5.

FIG. 7 is an isometric view showing how the erectometer of the present invention measures rigidity and tumescence when a sleep erection occurs.

DETAILED DESCRIPTION OF THE PREFERRED EMBODIMENT

FIG. 1 depicts a top plan view of the plural-characteristic-measuring radial erectometer of the present invention, made in accordance with its preferred embodiment and indicated at 10. While it may be made from any suitable material, erectometer 10 is preferably made from paper and preferably formed by following a conventional die-cutting process.

Referring to FIGS. 1-4, erectometer 10 includes elongate band-like structure 12 positionable around a patient's, or user's, flaccid penis, such as penis 14 (shown in cross section in FIG. 4). Band-like structure 12 is constructed to form a closed loop having a desired circumference corresponding to flaccid penis 14. Referring to FIGS. 1 and 3, the band-like structure also includes a central region 12a and a cushion region 12b, the importance of which will be described. Cushion region 12b may be formed by adhering a foam pad to the underside of band-like structure 12. Erectometer 10 also includes first measurement structure 16 that forms a first end of band-like structure 12 and is manually movable to a first configuration $FMS_1$ (FIG. 4) providing an indication that the penis is in a flaccid condition. As will be described, measurement structure 16 is also radially changeable to a second configuration $FMS_2$ as a result of radial-penile forces, such as those shown by arrows at 18 in FIG. 7, that will occur when a penis such as penis 14 becomes erect (see FIG. 7).

Referring to FIGS. 1-3, band-like structure 12 includes a transverse slot 19 formed in central region 12a adjacent the first end. First measurement structure 16 is preferably constructed as a detachable tab 20. Referring especially to FIG. 1, tab 20 includes a detachment region 22 that is detachably connected to the band-like structure in central region 12a and at opposing connect locations along its width W. Each connect location is outward of the central region, and the tab terminates with a fastener region 24 (FIG. 2) that is attachable to second measurement structure that will be described immediately below. Detachable tab 20 also includes plural spaced leg subregions, such as those shown at 20a, each being located adjacent a corresponding connect location shown inside circles 20c (see FIGS. 1 and 5). Referring for a moment to FIGS. 1-5, the reader's attention is drawn to circles 20c (FIGS. 1 and 5) which each show a connect location bounded by a notch 21 in band-like structure 12 (FIGS. 3-5) and the inner boundary of a corresponding leg subregion 20a. For reasons to be described, each connect location is bounded by a distance, or width, of about 0.02-inches. That is, there is about a 0.02-inch distance between the innermost point of each notch 21 and the lowest point of the inner boundary of a corresponding leg subregion.

Still referring to FIGS. 1–3, each leg subregion 20a is constructed to direct to the connect locations the to-be-described, radial-penile forces caused by an erect condition of penis 14. Referring back to FIG. 1, band-like structure 12 also includes visual indicator structure 26 that is constructed to direct the patient's attention to slot 19.

Referring to FIGS. 1–4, second measurement structure is shown at 28 and is preferably constructed as an elongate strip forming a second end of band-like structure 12, and terminating in an insert region 28a. Second measurement structure, or strip, 28 is manually movable to a first configuration SMS₁ (FIG. 4) providing an indication that penis 14 is in the flaccid condition. Referring to FIG. 1, the strip includes plural virtually-perceptible gradations 30 at desired locations along its length. Insert region 28a is feedable through slot 19 to move strip 28 to first configuration SMS₁. The strip is also radially changeable from first configuration SMS₁ to a second configuration SMS₂ (FIG. 7) as a result of the erection-caused, radial-penile forces (indicated by arrows 18 in FIG. 7).

As will be further described below, the fixed placement of tab 20 will mark first configuration SMS₁ where the tab is detachably connected to band-like structure 12. Observance of gradations between first configuration SMS₁ and second configuration SMS₂ provides a visual indication that penis 14 changed from the flaccid condition (FIG. 4) to the erect condition (FIG. 7).

Preferably, erectometer 11) is constructed with tab 16 constructed to measure penile rigidity, and with strip 28 constructed to measure penile tumescence. Of course it should be understood that the present invention includes the use of other types of radial measurement structure.

OPERATION AND PREFERRED METHOD OF PRACTICING

Referring to FIGS. 5–6, the patient wraps erectometer 10 around a desired location of his penis 14 (preferably just inward of the glans) and places insert region 28a through slot 19. Then the patient pulls insert region through slot 19 (FIG. 6) a desired distance so that erectometer 10 forms a closed loop (FIG. 4) having a desired circumference corresponding to flaccid penis 14. The patient is now ready to go to sleep with erectometer 10 having tab 20 in first configuration FMS₁, and strip 28 in first configuration SMS₁. The tab is attachable to an outer surface of strip 28 via fastener region 24 (FIGS. 2, 4). The presently preferred choice for fastener region 24 is an adhesive that may be wetted to adhere to strip 28.

FIG. 7 illustrates what occurs when penis 14 changes from the flaccid condition (FIG. 4) to an erect condition. Radial-penile forces, depicted generally by arrows 18, cause tab 20 to detach from band-like structure 12, thereby changing its configuration from first configuration FMS₁ (FIG. 4) to second configuration FMS₂. Those same radial-penile forces will cause strip 28 to slide a distance through slot 19, thereby changing strip 28 from first configuration SMS₁ (FIG. 4) to second configuration SMS₂ (FIG. 7). Referring to FIG. 7, the reader should recognize leg subregions 20a, due to their fixed attachment to strip 28 via fastener region 24, also provide an automatic, convenient marker corresponding to first configuration SMS₁ of strip 28. Referring to FIG. 7, second configuration SMS₂ of strip 28 can be marked by the patient when he awakes by folding back against the strip that section of it extending from slot 19.

Still referring to FIG. 7, leg subregions 20a direct to the connect locations the radial-penile forces caused by the depicted, erect condition of penis 14. The leg subregions thereby promote detachment at the connect locations and deter detachment or tearing of the band-like region adjacent slot 19 formed in its central region 12a.

It should be understood that measurements using erectometer 10 are designed to provide qualitative, not quantitative information about penile rigidity, tumescence and other desired characteristics. In addition, those skilled in the art know that the radial-penile force required to detach leg subregions 20a of tab 20 is a matter of design choice. The presently preferred way to preselect such force is by making erectometer 10 using paper with a thickness of 0.006-inches, and by constructing the connect locations (shown inside circle 20c in FIGS. 1 and 5) each with widths of about 0.02-inches.

It should also be understood that the rigidity characteristic referred to above may also be thought of as a threshold-circumference characteristic in which the threshold circumference is defined by the circumference corresponding to the penis in its flaccid condition (for example, FIG. 4). Referring to FIG. 7, when tab 20 detaches from band-like structure 12, it could be said that penis 14 either exceeds a preselected rigidity threshold or a preselected threshold-circumference characteristic.

With respect to packaging erectometer 10, the presently preferred method will be to pre-feed insert region 28a through slot 19 a desired preselected amount that is less than would be required by a patient. In other words, erectometer 10 is preferably packaged in a closed-loop configuration somewhat like that shown in FIG. 4. However, the loop will be larger than that shown in FIG. 4, and fastener region 24 will not be attached to strip 28.

From the above description it should be understood that the invention accomplishes the above objects by providing a comfortable, reliable device for determining the occurrence of a sleep erection that measures plural characteristics of that erection. Erectometer 10 also provides a device that provides for reliable, accepted methods of measuring both the rigidity and tumescence of an erect penis. In addition, the erectometer of the present invention is extremely comfortable to wear, unobtrusive to the patient during sleep, and does not require positioning on a relatively large portion of the penis. Erectometer 10 also provides for measurement of both penile rigidity and tumescence as a function of radial-penile forces caused by the sleep erection. It is also easily detachable from the penis after the latter returns to a flaccid condition following a sleep erection. The present invention is also easily and cost-effectively manufactured as by a conventional die-cutting operation.

Accordingly, while a preferred embodiment of the invention has been described herein, it is appreciated that modifications are possible that are within the scope of the invention.

It is claimed and desired to secure by Letters Patent:

1. An integrated plural-characteristic-measuring radial erectometer to be worn by a male user, comprising:
   elongate band-like structure positionable around the user's flaccid penis and constructed to form a closed loop having a desired circumference corresponding to such flaccid penis;

first measurement structure forming part of the band-like structure and being constructed to measure penile rigidity, and being manually movable to a first configuration providing an indication that the penis is in a flaccid condition, and being radially changeable to a second configuration as a result of radial-penile forces that will occur when the penis becomes erect, with correlation between the first and second configuration providing an indication that the penis changed from such flaccid condition to an erect condition, and providing a measurement of a first characteristic of that erect condition;

second measurement structure also forming part of the band-like structure and being constructed to measure penile tumescence, and being manually movable to a first configuration providing an indication that the penis is in such flaccid condition, and being radially changeable to a second configuration as a result of the erection-caused radial-penile forces, with correlation between the first and second configuration providing an indication that the penis changed from such flaccid condition to an erect condition, and providing a measurement of a second characteristic of that condition; and wherein the first measurement structure includes marker substructure also forming part of the band-like structure, with the marker substructure constructed to identify on the erectometer the first configuration of the second measurement structure, thereby accommodating automatic correlation between the first and second configuration of the second measurement structure.

2. The erectometer of claim 1, wherein the band-like structure has first and second ends and a width, and further includes a transverse slot formed in a central region of it adjacent the first end, and wherein the second measurement structure is constructed as an elongate strip forming the second end and terminating in an insert region, with the strip including visually perceptible gradations at desired locations along its length, and with the insert region being feedable through the slot to allow movement of the second measurement structure to its first configuration, and with the strip being radially changeable from its first configuration to its second configuration as a result of the erection-caused, radial-penile forces, with observance of gradations corresponding to the first and second configuration providing a visual indication that the penis changed from such flaccid condition to the erect condition, and providing a measurement of penile tumescence associated with that condition.

3. The erectometer of claim 2 wherein the marker substructure is formed as part of the fastener region of the detachable tab.

4. A plural-characteristic-measuring radial erectometer to be worn by a male user, comprising:

elongate band-like structure positionable around the user's flaccid penis and constructed to form a closed loop having a desired circumference corresponding to such flaccid penis, wherein the band-like structure has first and second ends and a width, and further includes a transverse slot formed in a central region of the band-like structure adjacent the first end;

first measurement structure being formed as part of the band-like structure and being constructed to measure penile rigidity, the first measurement structure being manually movable to a first configuration providing an indication that the penis is in a flaccid condition, and being radially changeable to a second configuration as a result of radial-penile forces that will occur when the penis becomes erect, wherein the first measurement structure is constructed as a detachable tab forming the first end of the band-like structure, with the tab including a detachment region being detachably connected to the band-like structure at opposing connect locations along its width, and with each location being outward of the central region, and with the tab terminating with a fastener region that is attachable to the strip for manually moving the tab to a first configuration when the strip is moved to its first configuration, and with the detachment region being constructed to detach from the opposing locations and change to a second configuration as a result of such erection-caused radial-penile forces, with correlation between the first and second configurations of the tab providing a visual indication that the penis changed from such flaccid condition to the erect condition, thereby to measure penile rigidity associated with that condition;

second measurement structure being constructed to measure penile tumescence, the second measurement structure being manually movable to a first configuration providing an indication that the penis is in such flaccid condition, and being radially changeable to a second configuration as a result of the erection-caused radial-penile forces, the second measurement structure being constructed as an elongate strip forming the second end of the band-like structure and terminating in an insert region, with the strip including visually perceptible gradations at desired locations along its length, and with the insert region being feedable through the slot to allow movement of the second measurement structure to its first configuration, and with the strip being radially changeable from its first configuration to its second configuration as a result of the erection-caused, radial-penile forces, with observance of gradations corresponding to the first and second configuration providing a visual indication that the penis changed from such flaccid condition to the erect condition, thereby to measure penile tumescence associated with that condition.

5. The erectometer of claim 4, wherein the detachable tab is constructed with plural spaced leg subregions, each being located adjacent a corresponding connect location, and with each leg subregion being constructed to direct at the connect locations the radial-penile forces caused by the erect condition, thereby promoting detachment at the connect locations and deterring detachment or tearing of the band-like region adjacent the slot formed in its central region.

* * * * *